United States Patent
Ranpura et al.

(10) Patent No.: US 8,690,793 B2
(45) Date of Patent: Apr. 8, 2014

(54) BIOPSY DEVICE HAVING ROTATIONAL CUTTING

(75) Inventors: Himanshu M. Ranpura, Laveen, AZ (US); Angela K. Jensen, Mesa, AZ (US); Kenneth Shane Guillory, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 209 days.

(21) Appl. No.: 13/254,109

(22) PCT Filed: Mar. 16, 2009

(86) PCT No.: PCT/US2009/037289
§ 371 (c)(1),
(2), (4) Date: Aug. 31, 2011

(87) PCT Pub. No.: WO2010/107424
PCT Pub. Date: Sep. 23, 2010

(65) Prior Publication Data
US 2011/0313316 A1 Dec. 22, 2011

(51) Int. Cl.
*A61B 10/00* (2006.01)
(52) U.S. Cl.
USPC .......... 600/562; 600/564; 600/565; 600/566; 600/567; 600/568
(58) Field of Classification Search
USPC .............. 600/562, 564, 565, 566, 567, 568
See application file for complete search history.

(56) References Cited

U.S. PATENT DOCUMENTS

| | | |
|---|---|---|
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |

(Continued)

FOREIGN PATENT DOCUMENTS

| | | |
|---|---|---|
| CN | 101011268 A | 8/2007 |
| CN | 101032420 A | 9/2007 |

(Continued)

*Primary Examiner* — Rene Towa
*Assistant Examiner* — May Abouelela

(57) ABSTRACT

A biopsy device includes a probe assembly and a driver unit. The probe assembly includes a first cannula having a first aperture extending to a lumen proximal to a first distal end of the first cannula. A second cannula has a second aperture extending to a lumen proximal to the second distal end of the second cannula. The second cannula is disposed co-axially with the first cannula. A least one of the first aperture and the second aperture has a cutting edge. The driver unit is configured for releasably mounting the probe assembly. The driver unit is operatively configured to simultaneously rotate the first cannula and the second cannula at different rotational velocities so that the first aperture and the second aperture periodically come into alignment to form a virtual tissue sample aperture.

27 Claims, 8 Drawing Sheets

(56) References Cited

U.S. PATENT DOCUMENTS

| | | |
|---|---|---|
| 3,800,783 A | 4/1974 | Jamshidi |
| 3,844,272 A * | 10/1974 | Banko ........................... 600/566 |
| 3,882,849 A | 5/1975 | Jamshidi |
| 3,889,682 A | 6/1975 | Denis et al. |
| 3,996,935 A | 12/1976 | Banko |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,282,476 A | 2/1994 | Terwilliger |
| 5,282,477 A | 2/1994 | Bauer |
| 5,290,253 A | 3/1994 | Kira |
| 5,324,306 A | 6/1994 | Makower et al. |
| 5,334,183 A | 8/1994 | Wuchinich |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A * | 6/1996 | Burbank et al. ............... 600/567 |
| 5,535,755 A | 7/1996 | Heske |
| 5,546,957 A | 8/1996 | Heske |
| 5,554,151 A | 9/1996 | Hinchliffe |
| 5,560,373 A | 10/1996 | DeSantis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,585 A | 2/1997 | Banik et al. |
| 5,602,449 A * | 2/1997 | Krause et al. ............. 318/400.09 |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A * | 7/1999 | Burbank et al. ............... 600/567 |
| 5,944,673 A | 8/1999 | Gregoire et al. |
| 5,951,490 A | 9/1999 | Fowler |
| 5,951,575 A | 9/1999 | Bolduc et al. |
| 5,964,716 A * | 10/1999 | Gregoire et al. ............... 600/564 |
| 5,971,939 A | 10/1999 | DeSantis et al. |
| 5,976,164 A | 11/1999 | Bencini et al. |
| 5,980,469 A * | 11/1999 | Burbank et al. ............... 600/567 |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A * | 6/2000 | Gregoire et al. ............... 600/566 |
| 6,083,176 A | 7/2000 | Terwilliger |
| 6,083,237 A | 7/2000 | Huitema et al. |
| 6,086,544 A * | 7/2000 | Hibner et al. .................. 600/568 |
| 6,106,484 A | 8/2000 | Terwilliger |
| 6,110,129 A | 8/2000 | Terwilliger |
| 6,120,462 A | 9/2000 | Hibner |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |

(56) References Cited

U.S. PATENT DOCUMENTS

| | | |
|---|---|---|
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1* | 8/2001 | Privitera et al. ............... 600/568 |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,860,860 B2 | 3/2005 | Viola |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2* | 4/2006 | Thompson et al. ............ 600/564 |
| D525,583 S | 7/2006 | Vu |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2* | 10/2010 | Beckman et al. ............. 600/566 |
| 7,828,746 B2 | 11/2010 | Teague |
| 7,846,109 B2* | 12/2010 | Parihar et al. ................. 600/567 |
| 7,854,706 B2* | 12/2010 | Hibner ........................ 600/566 |
| 7,862,517 B2 | 1/2011 | Tsonton et al. |
| 7,862,518 B2* | 1/2011 | Parihar ........................ 600/567 |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2* | 6/2011 | McCullough et al. ........ 600/566 |
| 7,974,681 B2 | 7/2011 | Wallace et al. |
| 8,012,102 B2* | 9/2011 | McCullough et al. ........ 600/566 |
| 8,016,844 B2 | 9/2011 | Privitera et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,687 B2* | 12/2011 | Parihar ........................ 600/568 |
| 8,118,755 B2* | 2/2012 | Hibner et al. ................. 600/565 |
| 8,152,738 B2 | 4/2012 | Li et al. |
| 8,172,771 B2 | 5/2012 | Miller et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2* | 8/2012 | Speeg et al. .................. 600/565 |
| 8,251,917 B2* | 8/2012 | Almazan ...................... 600/566 |
| 8,262,586 B2* | 9/2012 | Anderson et al. ............. 600/567 |
| 8,267,868 B2* | 9/2012 | Taylor et al. .................. 600/564 |
| 8,277,393 B2* | 10/2012 | Miller et al. .................. 600/567 |
| 8,282,574 B2* | 10/2012 | Coonahan et al. ............ 600/564 |
| 8,287,465 B2* | 10/2012 | Hardin et al. ................. 600/565 |
| 8,313,444 B2* | 11/2012 | Thompson et al. ........... 600/568 |
| 8,343,069 B2 | 1/2013 | Uchiyama et al. |
| 8,430,825 B2 | 4/2013 | Mark |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1* | 10/2002 | Neuenfeldt ................... 600/564 |
| 2002/0156395 A1 | 10/2002 | Stephens et al. |
| 2003/0023188 A1 | 1/2003 | Kritzman et al. |

(56) References Cited

U.S. PATENT DOCUMENTS

| | | |
|---|---|---|
| 2003/0023239 A1* | 1/2003 | Burbank et al. ............... 606/45 |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1* | 2/2004 | Privitera et al. ............... 600/170 |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0167428 A1* | 8/2004 | Quick et al. ............... 600/564 |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0249278 A1 | 12/2004 | Krause |
| 2004/0249307 A1* | 12/2004 | Thompson et al. ............ 600/568 |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1* | 3/2005 | Shabaz et al. ............... 600/564 |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1* | 9/2005 | Hibner et al. ............... 600/566 |
| 2005/0275378 A1 | 12/2005 | Canino et al. |
| 2005/0277829 A1* | 12/2005 | Tsonton et al. ............... 600/423 |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0122535 A1* | 6/2006 | Daum ............... 600/565 |
| 2006/0129063 A1 | 6/2006 | Thompson et al. |
| 2006/0149162 A1* | 7/2006 | Daw et al. ............... 600/564 |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1* | 1/2007 | Feldman et al. ............... 600/567 |
| 2007/0032741 A1 | 2/2007 | Hibner et al. |
| 2007/0032743 A1* | 2/2007 | Hibner ............... 600/566 |
| 2007/0055173 A1* | 3/2007 | DeLonzor et al. ............ 600/564 |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0161925 A1 | 7/2007 | Quick et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1* | 8/2007 | Hibner ............... 600/567 |
| 2007/0213590 A1 | 9/2007 | Squicciarini |
| 2007/0213630 A1* | 9/2007 | Beckman et al. ............... 600/562 |
| 2007/0213632 A1* | 9/2007 | Okazaki et al. ............... 600/562 |
| 2007/0219572 A1 | 9/2007 | Deck et al. |
| 2007/0236180 A1 | 10/2007 | Rodgers |
| 2007/0239067 A1* | 10/2007 | Hibner et al. ............... 600/567 |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0103411 A1* | 5/2008 | Van Bladel et al. ............ 600/564 |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1* | 12/2008 | Taylor et al. ............... 600/567 |
| 2009/0030405 A1 | 1/2009 | Quick et al. |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0125062 A1 | 5/2009 | Arnin |
| 2009/0137927 A1 | 5/2009 | Miller |
| 2009/0171242 A1* | 7/2009 | Hibner ............... 600/566 |
| 2009/0171243 A1 | 7/2009 | Hibner et al. |
| 2009/0204022 A1 | 8/2009 | Schwindt |
| 2009/0227893 A1* | 9/2009 | Coonahan et al. ............... 600/566 |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152610 A1* | 6/2010 | Parihar et al. ............... 600/566 |
| 2010/0152611 A1 | 6/2010 | Parihar et al. ............... 600/566 |
| 2010/0160820 A1 | 6/2010 | Weikel, Jr. et al. |
| 2010/0160823 A1* | 6/2010 | Parihar et al. ............... 600/567 |
| 2010/0210966 A1 | 8/2010 | Videbaek |
| 2010/0234760 A1 | 9/2010 | Almazan |
| 2010/0292607 A1* | 11/2010 | Moore et al. ............... 600/566 |
| 2010/0312140 A1 | 12/2010 | Smith et al. |
| 2010/0317995 A1 | 12/2010 | Hibner et al. |

(56) References Cited

U.S. PATENT DOCUMENTS

| | | |
|---|---|---|
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0224577 A1* | 9/2011 | Park .................. 600/567 |
| 2012/0130275 A1* | 5/2012 | Chudzik et al. ........ 600/567 |
| 2012/0191009 A1 | 7/2012 | Hoon et al. |
| 2012/0215130 A1 | 8/2012 | Field et al. |

FOREIGN PATENT DOCUMENTS

| | | |
|---|---|---|
| DE | 3924291 A1 | 1/1991 |
| DE | 4041614 C1 | 10/1992 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0995400 A1 | 4/2000 |
| EP | 1074271 A2 | 2/2001 |
| EP | 1520518 A2 | 4/2005 |
| EP | 1665989 A2 | 6/2005 |
| EP | 1579809 A1 | 9/2005 |
| EP | 1604615 A1 | 12/2005 |
| EP | 1829487 A1 | 9/2007 |
| EP | 2095772 A1 | 2/2009 |
| EP | 2106750 A1 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |
| WO | 2010120294 A1 | 10/2010 |
| WO | 2011019343 A1 | 2/2011 |

* cited by examiner

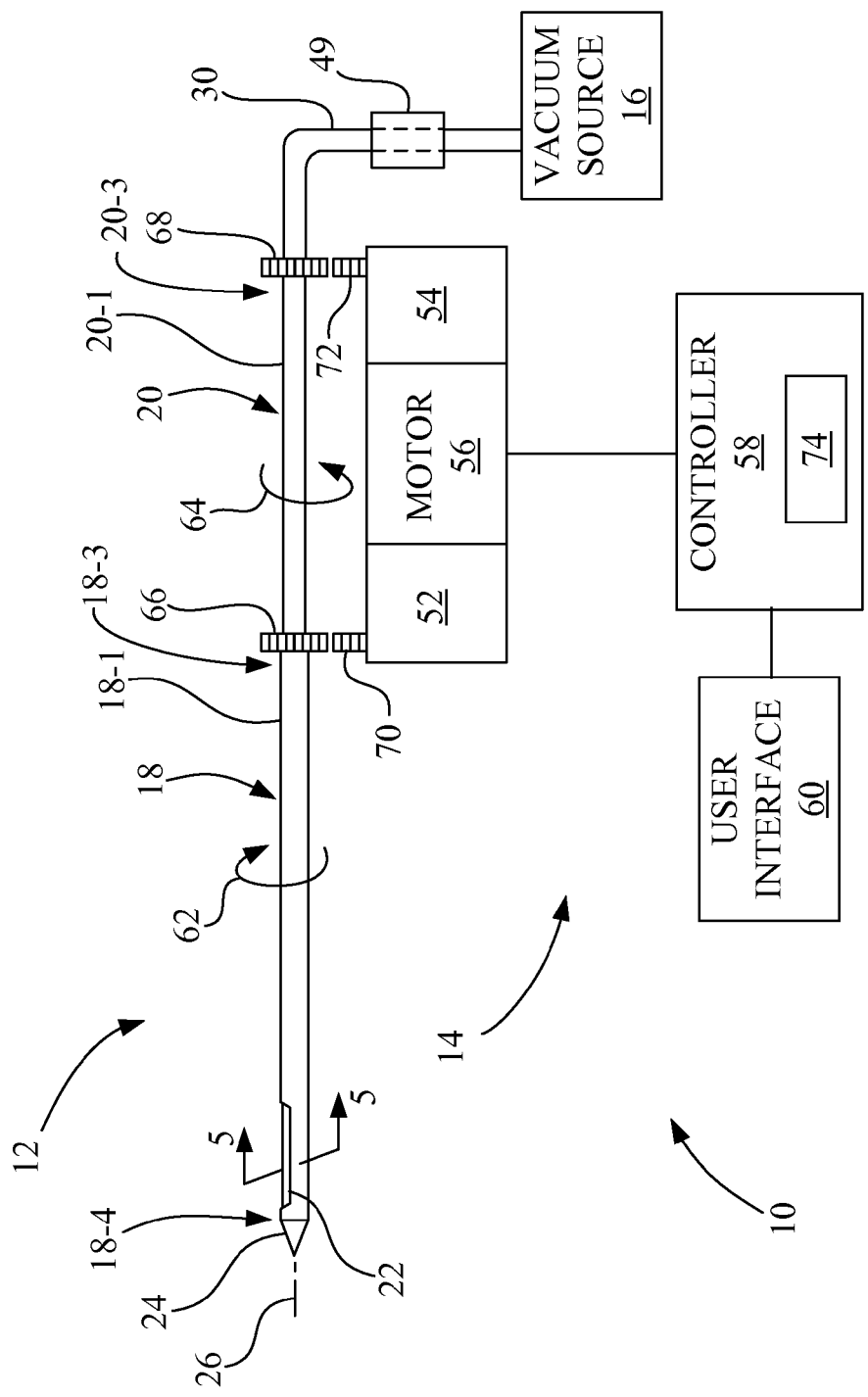

BIOPSY DEVICE HAVING ROTATIONAL CUTTING

CROSS REFERENCE TO RELATED APPLICATIONS

This application is a U.S. national phase of International Application No. PCT/US2009/037289, filed Mar. 16, 2009, from which priority is claimed and which is incorporated herein by reference in its entirety.

BACKGROUND OF THE INVENTION

1. Field of the Invention

The present invention relates to medical devices, and, more particularly, to a biopsy device having rotational cutting.

2. Description of the Related Art

A typical biopsy device includes a probe assembly having a cannula configured with a sample notch and a tissue sampling chamber and associated tissue cutting mechanism. During a biopsy procedure, vacuum assistance may be used to help draw tissue through the sample notch and into the sampling chamber and maximize the amount of tissue obtained with each sample. Some biopsy devices, commonly referred to as single insertion, multiple samples, or SIMS devices, utilize sample acquisition and delivery mechanisms that allow multiple samples to be acquired from a given lesion without removing and reinserting the needle after each sample. One type of cutting mechanism used in a vacuum assisted SIMS biopsy device uses rotational and linear motion of a cutter with respect to the sample notch to sever the tissue drawn through the sample notch into the tissue sampling chamber. Vacuum is applied to transport the tissue from the sampling chamber to a sample collection basket. This process may be repeated until the desired amount of tissue has been obtained.

In one common SIMS biopsy device, it is necessary for an operator to manually rotate the probe assembly to different orientations after each sample in order to obtain tissue samples at different radial orientations within the target site. However, in some situations, such manual rotation may be inconvenient.

SUMMARY OF THE INVENTION

The present invention provides a biopsy device and method for obtaining biopsy samples, wherein the biopsy device is configured to periodically form a virtual tissue sample aperture at a plurality of angular radial positions.

In the description of the invention that follows, the terms "first" and "second" preceding an element name are used for identification purposes to distinguish between similar or related elements, results or concepts, and are not intended to necessarily imply order, nor are the terms "first" and "second" intended to preclude the inclusion of additional similar or related elements, results or concepts, unless otherwise indicated.

The invention, in one form thereof, is directed to a biopsy device including a probe assembly and a driver unit. The probe assembly includes a first cannula having a first side wall defining a first lumen. The first cannula has a first proximal end and a first distal end. The first cannula has a first aperture extending through the first side wall to the first lumen proximal to the first distal end. The first cannula has a longitudinal axis. A second cannula has a second side wall defining a second lumen. The second cannula has a second proximal end and a second distal end. The second cannula has a second aperture extending through the second side wall to the second lumen proximal to the second distal end. The second cannula is disposed co-axially with the first cannula. A least one of the first aperture and the second aperture has a cutting edge. The driver unit is configured for releasably mounting the probe assembly. The driver unit is operatively configured to simultaneously rotate the first cannula and the second cannula in opposite rotational directions at different rotational velocities so that the first aperture and the second aperture periodically come into alignment to form a virtual tissue sample aperture.

The invention, in another form thereof, is directed to a biopsy device including a probe assembly and a driver unit. The probe assembly includes a first cannula having a first side wall defining a first lumen. The first cannula has a first proximal end and a first distal end. The first cannula has a first aperture extending through the first side wall to the first lumen proximal to the first distal end. The first cannula has a longitudinal axis. A second cannula has a second side wall defining a second lumen. The second cannula has a second proximal end and a second distal end. The second cannula has a second aperture extending through the second side wall to the second lumen proximal to the second distal end. The second cannula is disposed co-axially with the first cannula. At least one of the first aperture and the second aperture has a cutting edge. The driver unit is configured for releasably mounting the probe assembly. The driver unit is operatively configured to rotate the first cannula in accordance with a first velocity profile and the second cannula in accordance with a second velocity profile to periodically align the first aperture and the second aperture to form a virtual tissue sample aperture at a plurality of angular radial positions relative to the longitudinal axis during a biopsy procedure by continuous simultaneous rotation of both of the first cannula and the second cannula.

The invention, in another form thereof, is directed to a method for controlling a biopsy device during a biopsy procedure, the biopsy device having a probe assembly with an outer cannula having a distal needle tip and an inner cannula arranged coaxial with the outer cannula with respect to a longitudinal axis, the outer cannula having a first side aperture and the inner cannula having a second side aperture with at least one of the first side aperture and the second side aperture having a cutting edge, and a vacuum source connected in fluid communication with a lumen of the inner cannula and with a tissue sample receptacle. The method includes positioning each of the outer cannula and the inner cannula at a respective initial rotational position; inserting the probe assembly in a region of a patient to be biopsied; establishing continuous simultaneous rotation of the outer cannula in accordance with a first velocity profile and the inner cannula in accordance with a second velocity profile to periodically align the first side aperture and the second side aperture to form a virtual tissue sample aperture at a plurality of angular radial positions relative to the longitudinal axis; establishing a supply of negative pressure in the lumen of the inner cannula, such that each time the virtual tissue sample aperture is formed tissue is pulled through the virtual tissue sample aperture into the lumen of the inner cannula, and thereafter the first side aperture and the second side aperture cooperate to sever the tissue that is pulled into the inner cannula as the virtual tissue sample aperture is closed by the continuous simultaneous rotation of the outer cannula and the inner cannula, each tissue sample so severed being transported through the lumen of the inner cannula by the negative pressure to a tissue sample receptacle; and ceasing the continuous simultaneous rotation of the outer cannula and the inner cannula after all desired tissue samples have been harvested.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a pictorial illustration of a biopsy device including a probe assembly and driver unit, configured in accordance with an embodiment of the present invention.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 2A:
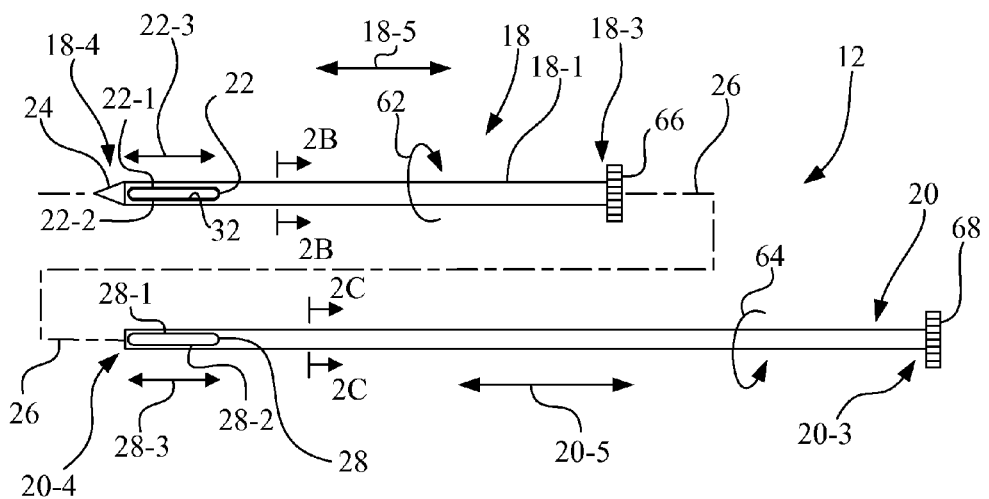
FIG. 2A is an exploded view of the probe assembly of FIG. 1.
Figures 2B, 2C:
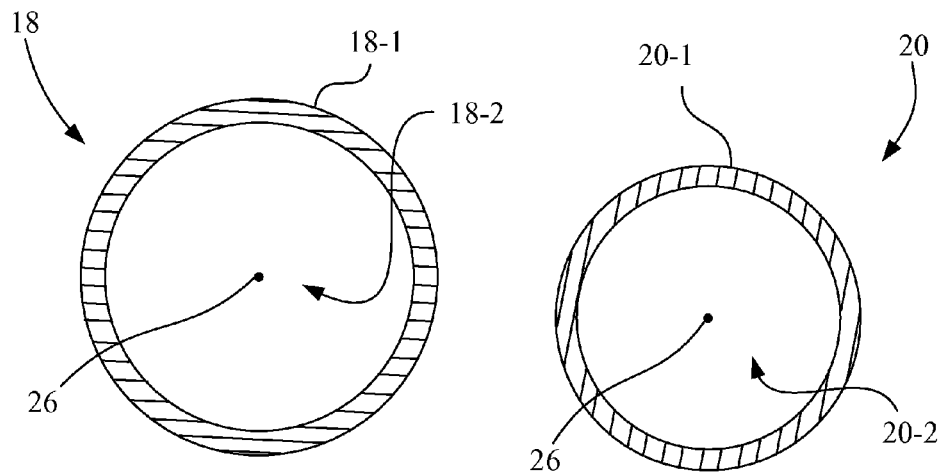
FIG. 2B is a cross-section view of the outer cannula of FIG. 2A taken along line 2B-2B.
FIG. 2C is a cross-section view of the inner cannula of FIG. 2A taken along line 2C-2C.

Referring now to the drawings and particularly to FIG. 1, there is shown a biopsy device 10 configured in accordance with an embodiment of the present invention. Biopsy device 10 includes a probe assembly 12, a driver unit 14, and a vacuum source 16.

Referring also to FIGS. 2A-2C, 3, 4, and 5, probe assembly 12 includes an outer cannula 18 and an inner cannula 20.

Outer cannula 18 has a first side wall 18-1 defining a first lumen 18-2. Outer cannula 18 has a first proximal end 18-3, a first distal end 18-4, and a first aperture 22 extending through first side wall 18-1 to the first lumen 18-2 at a location proximal to first distal end 18-4. A needle tip 24 is located at first distal end 18-4 of outer cannula 18. A longitudinal axis 26 of probe assembly 12 passes centrally through first lumen 18-2 of outer cannula 18 parallel to a longitudinal extent 18-5 of outer cannula 18.

Inner cannula 20 is disposed co-axially with outer cannula 18 with respect to longitudinal axis 26. Inner cannula 20 has a second side wall 20-1 defining a second lumen 20-2. Inner cannula 20 has a second proximal end 20-3, a second distal end 20-4, and a second aperture 28 extending through second side wall 20-1 to second lumen 20-2 at a location proximal to second distal end 20-4. Longitudinal axis 26 of probe assembly 12 passes centrally through second lumen 20-2 of inner cannula 20 parallel to a longitudinal extent 20-5 of inner cannula 20.

Vacuum source 16 is in fluid communication with inner cannula 20 via a fluid conduit 30, and may establish a continuous or intermittent negative pressure in second lumen 20-2 of inner cannula 20.

In the present embodiment as shown in FIGS. 1 and 2, first aperture 22 has a longitudinal edge 22-1 spaced apart from a longitudinal edge 22-2, with a longitudinal extent 22-3 of first aperture 22 being parallel to longitudinal axis 26. Second aperture 28 has a longitudinal edge 28-1 spaced apart from a longitudinal edge 28-2, with a longitudinal extent 28-3 of second aperture 28 being parallel to longitudinal axis 26. At least one of first aperture 22 of outer cannula 18 and second aperture 28 of inner cannula 20 has a cutting edge 32 that is sharpened to razor sharpness. For example, cutting edge 32 may be formed on one or more of longitudinal edges 22-1, 22-2, 28-1 and 28-2. Also, for example, the one or more of longitudinal edges 22-1, 22-2, 28-1 and 28-2 having cutting edge 32 may have an elliptical shape so that cutting edge 32 is correspondingly elliptical to aid in severing tissue.

FIGS. 6A-6C and 7 show another exemplary embodiment for a probe assembly 34 that may be substituted for probe assembly 12. Probe assembly 34 has an outer cannula 36 and an inner cannula 38.

Outer cannula 36 has a first side wall 36-1 defining a first lumen 36-2. Outer cannula 36 has a first proximal end 36-3, a first distal end 36-4, and a first aperture 40 extending through first side wall 36-1 to the first lumen 36-2 at a location proximal to first distal end 36-4. Needle tip 24 is located at first distal end 36-4 of outer cannula 36. Longitudinal axis 26 of probe assembly 34 passes centrally through first lumen 36-2 of outer cannula 36.

Inner cannula 38 is disposed co-axially with outer cannula 36 with respect to longitudinal axis 26. Inner cannula 38 has a second side wall 38-1 defining a second lumen 38-2. Inner cannula 38 has a second proximal end 38-3, a second distal end 38-4, and a second aperture 42 extending through second side wall 38-1 to second lumen 38-2 at a location proximal to second distal end 38-4. Longitudinal axis 26 of probe assembly 34 passes centrally through second lumen 38-2 of inner cannula 38.

Probe assembly 34 differs from probe assembly 12 only in the shape of apertures 40 and 42 relative to apertures 22, 28. Aperture 40 of outer cannula 36 has a longitudinal edge 40-1 spaced apart from a longitudinal edge 40-2, with a longitudinal extent 40-3 of aperture 40 being non-parallel, i.e., angled, with respect to longitudinal axis 26 at a first direction 40-4.

Aperture 42 of inner cannula 38 has a longitudinal edge 42-1 spaced apart from a longitudinal edge 42-2, with a longitudinal extent 42-3 of aperture 42 being non-parallel, i.e., angled, with respect to longitudinal axis 26 in a second direction 42-4 that intersects first direction 40-4 of aperture 40.

At least one of first aperture 40 of outer cannula 36 and second aperture 42 of inner cannula 38 has a cutting edge 44 that is sharpened to razor sharpness. For example, cutting edge 44 may be formed on one or more of longitudinal edges 40-1, 40-2, 42-1 and 42-2. The angled extent of the one or more of longitudinal edges 40-1, 40-2, 42-1 and 42-2 having cutting edge 44 aids in severing tissue.

Referring again to FIGS. 1, 2A and 6A, driver unit 14 is configured for releasably mounting probe assembly 12 or probe assembly 34. For brevity, unless otherwise indicated, the discussions that follow will describe the invention with reference to the components of probe assembly 12. However, it is to be understood that the discussion as applied to probe assembly 12 may be easily applied to the use of probe assembly 34 as a substitute for probe assembly 12, and thus for brevity will not be repeated.

Figure 3:
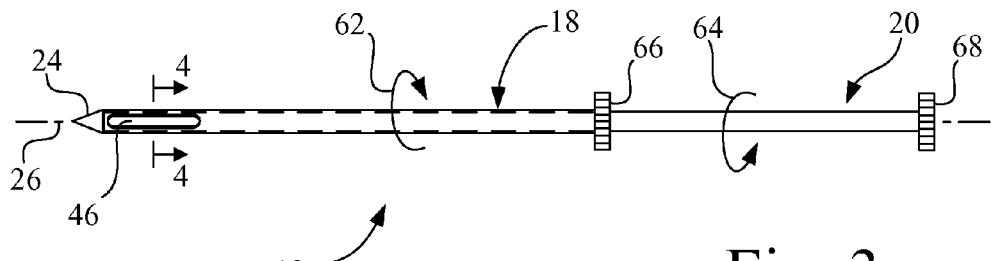
FIG. 3 is an assembled view of the probe assembly of FIG. 2A having the respective apertures of the outer cannula and inner cannula in alignment.
Figure 4:
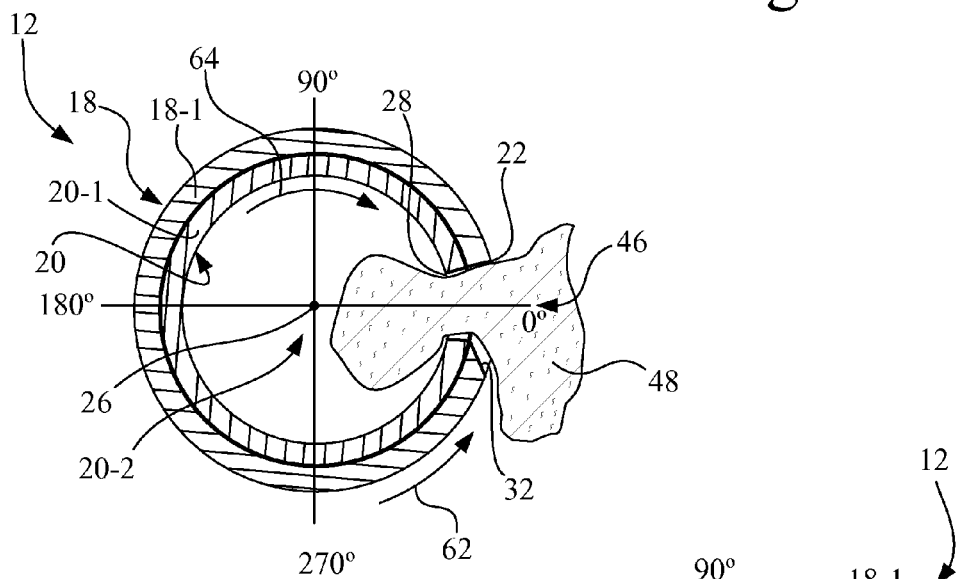
FIG. 4 is a cross-section view of the probe assembly of FIG. 3 taken along line 4-4, showing tissue being drawn through a virtual tissue sample aperture.

Referring to FIGS. 1-5, driver unit 14 is operatively configured to simultaneously rotate outer cannula 18 and inner cannula 20, which in one exemplary implementation are rotated in opposite rotational directions at different rotational velocities so that first aperture 22 and second aperture 28 periodically come into alignment to form a virtual tissue sample aperture 46, as illustrated in FIGS. 3 and 4. As more fully described below, virtual tissue sample aperture 46 may be formed at a plurality of angular radial positions relative to longitudinal axis 26 during a biopsy procedure by continuous simultaneous rotation of both of outer cannula 18 and inner cannula 20.

In the present embodiment, as shown in FIGS. 3 and 4, a maximum opening size of virtual tissue sample aperture 46 is equal to the smaller of a respective opening size for each of first aperture 22 of outer cannula 18 and second aperture 28 of inner cannula 20. In some implementations, it may be desirable for first aperture 22 and second aperture 28 to be of substantially the same size.

Each time a virtual tissue sample aperture 46 is formed, negative pressure established in second lumen 20-2 of inner cannula 20 by vacuum source 16 pulls surrounding tissue 48 that is adjacent to virtual tissue sample aperture 46 into inner cannula 20. Grooves or channels (not shown) may be placed in inner cannula 20 to allow vacuum to reach both sides of the tissue collection area in second lumen 20-2. Thereafter, the first aperture 22 of outer cannula 18 and second aperture 28 of inner cannula 20 cooperate to sever tissue 48 that is pulled into inner cannula 20 as virtual tissue sample aperture 46 is closed by the continued simultaneous rotation of outer cannula 18 and inner cannula 20. Each tissue sample so severed is transported through the second lumen 20-2 of inner cannula 20 by the negative pressure to a tissue sample receptacle 49.

Figure 6A:
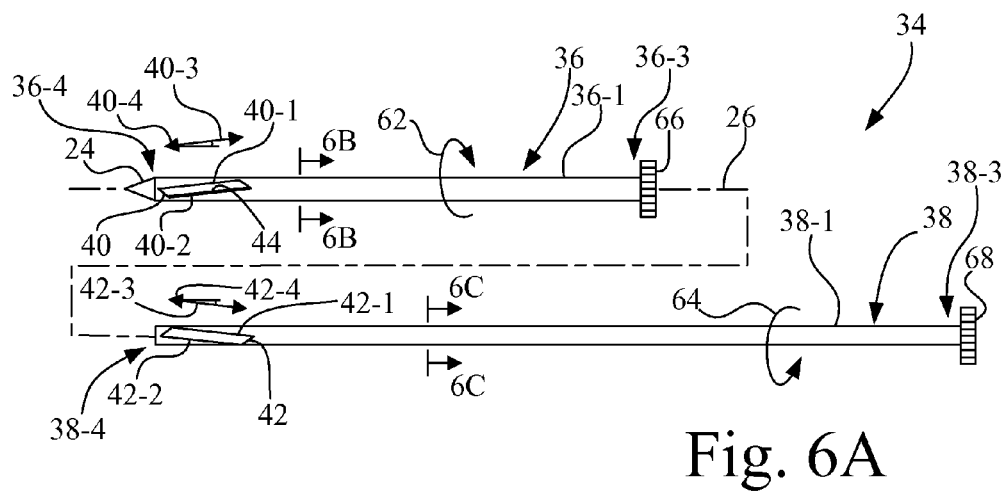
FIG. 6A is an exploded view of another embodiment for a probe assembly suitable for use in the biopsy device of FIG. 1.
Figures 6B, 6C:
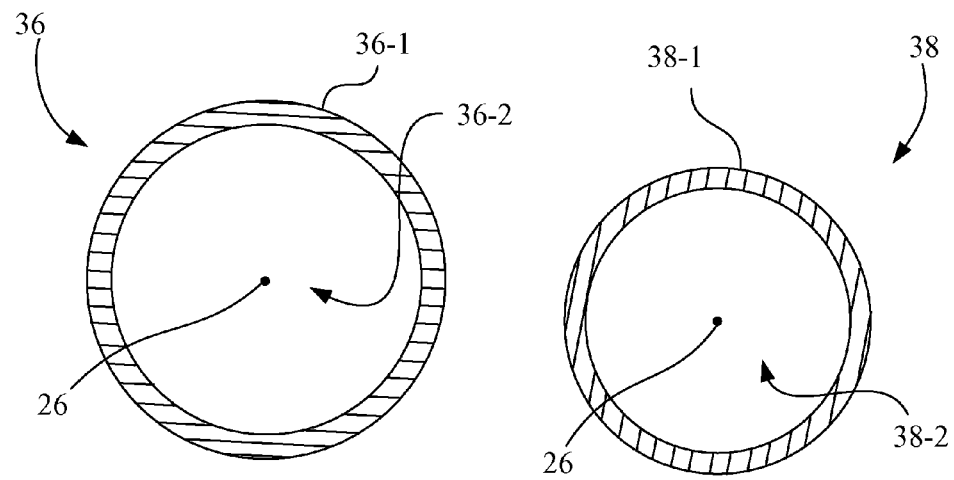
FIG. 6B is a cross-section view of the outer cannula of FIG. 6A taken along line 6B-6B.
FIG. 6C is a cross-section view of the inner cannula of FIG. 6A taken along line 6C-6C.
Figure 7:
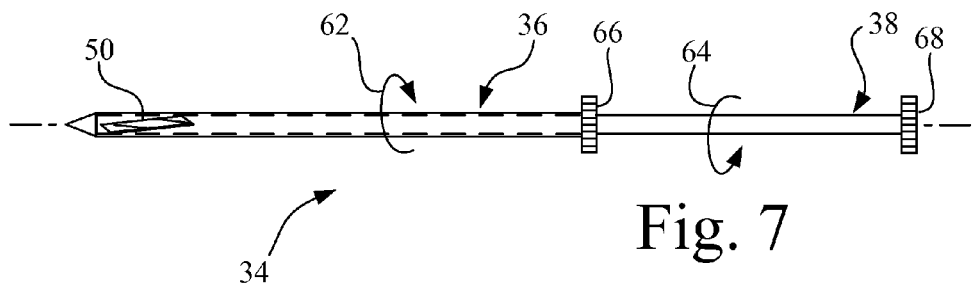
FIG. 7 is an assembled view of the probe assembly of FIG. 6A having the respective apertures of the outer cannula and inner cannula in alignment.

In the embodiment shown in FIGS. 6A-6C, with further reference to FIG. 7, probe assembly 34 including outer cannula 36 and inner cannula 38 may be installed on driver unit 14, and in a one implementation outer cannula 36 and inner cannula 38 may be rotated in opposite rotational directions at different rotational velocities so aperture 40 and aperture 42 periodically come into alignment to form a virtual tissue sample aperture 50, as illustrated in FIG. 7. In this embodiment as shown in FIGS. 6A-7, however, a maximum opening size of virtual tissue sample aperture 50 is less than an opening size of either of aperture 40 of outer cannula 36 and aperture 42 of inner cannula 38.

It is contemplated that other shapes may be used for the respective apertures, such as polygonal, circles, ellipses or combinations thereof.

Referring again to FIGS. 1-5, driver unit 14 includes a first drive mechanism 52, a second drive mechanism 54, a motor 56, a controller 58 and a user interface 60. First drive mechanism 52 is configured for drivable engagement with outer cannula 18 to rotate outer cannula 18 of probe assembly 12 at a first rotational velocity in a first rotational direction 62. Second drive mechanism 54 is configured for drivable engagement with the inner cannula 20 of probe assembly 12 to rotate inner cannula 20 at a second rotational velocity different from the first rotational velocity in a second rotational direction 64, opposite to the first rotational direction 62, simultaneously with the rotation of outer cannula 18.

More particularly, in the present embodiment as shown in FIGS. 1-3, a first gear 66 is fixedly attached to outer cannula 18 for rotation about longitudinal axis 26. A second gear 68 is fixedly attached to inner cannula 20 for rotation about longitudinal axis 26. First drive mechanism 52 may be in the form of a first gear drive mechanism 70 engaged first gear 66. Second drive mechanism 54 may be in the form of a second gear drive mechanism 72 engaged with second gear 68. Motor 56, such as a D.C. motor, is drivably coupled to each of first drive mechanism 52 (and in turn first gear drive mechanism 70) and second drive mechanism 54 (and in turn second gear drive mechanism 72).

In the present embodiment having a single motor 56 common to first drive mechanism 52 and second drive mechanism 54, the rotational velocity differences and rotational directions associated with outer cannula 18 and inner cannula 20, and in turn the angular radial positions of the formation of virtual tissue sample aperture 46 for harvesting the tissue samples, are predefined by the gearing in the gear drive mechanisms 70, 72 respectively of first drive mechanism 52 and second drive mechanism 54.

Controller 58 is communicatively coupled to user interface 60, such as a keypad, touch screen, foot-pedal, etc., and may be used to receive user input, such as the desired number of tissue samples to be taken, and to display status. Also, controller 58 is communicatively coupled to motor 56 and controls the speed of motor 56 in accordance with a motor velocity profile 74. As such, referring now also to FIG. 8, controller 58 is configured to control motor 56 to effect rotation of outer cannula 18 in accordance with a first velocity profile 76 and to effect rotation of inner cannula 20 in accordance with a second velocity profile 78.

Figure 8:
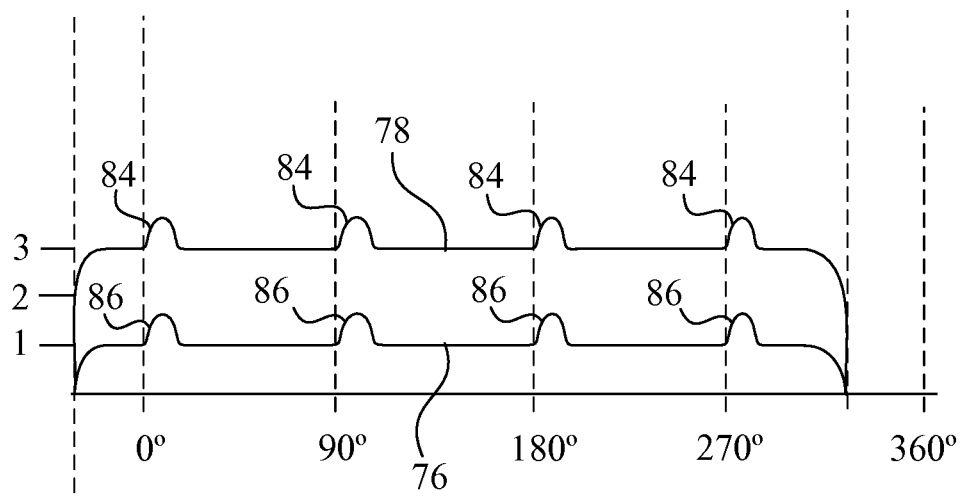
FIG. 8 is a graphical representation of exemplary velocity profiles for the outer cannula and the inner cannula of FIG. 1.
Figure 9:
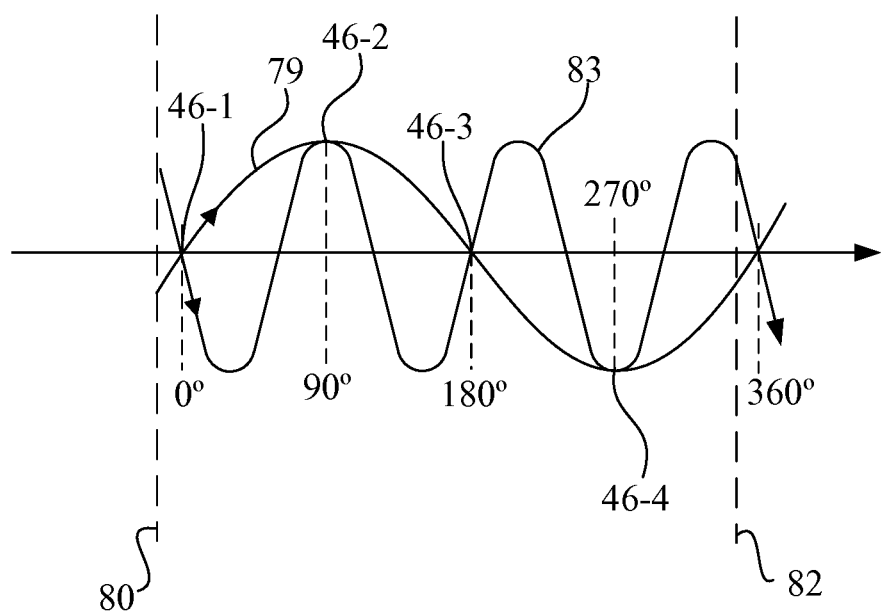
FIG. 9 is a graphical representation of the formation of a virtual tissue sample aperture at each of a plurality of angular radial positions.

In the present example, as illustrated in FIG. 8, the velocity magnitude of inner cannula 20 subject to velocity profile 78 is three times the velocity magnitude of outer cannula 18 subject to velocity profile 76, with outer cannula 18 and inner cannula 20 rotating in opposite directions. Accordingly, as illustrated in FIG. 9, a complete continuous rotation of outer cannula 18 as illustrated by waveform 79 from an initial position 80 (see also FIG. 5) to a final position 82 (see also FIG. 5), and a simultaneous counter rotation of inner cannula 20 at three times the velocity of that of outer cannula 18 as illustrated by waveform 83 from initial position 80 to a final position 82, results in the formation of a plurality of virtual tissue sample apertures 46 (see FIGS. 3 and 4), which in the present example virtual tissue sample apertures 46-1, 46-2, 46-3 and 46-4 are formed at angular radial positions relative to longitudinal axis 26 offset from one another at 90 degrees of rotation of outer cannula 18, resulting in four samples being harvested within one rotation of outer cannula 18. More particularly, in the example shown in FIG. 9, a virtual tissue sample aperture 46-1 is formed at 0 degrees, a virtual tissue sample aperture 46-2 is formed at 90 degrees, a virtual tissue sample aperture 46-3 is formed at 180 degrees and a virtual tissue sample aperture 46-4 is formed at 270 degrees.

Referring again to FIG. 8, first velocity profile 76 and second velocity profile 78 include an acceleration 84 of outer cannula 18 and an acceleration 86 of inner cannula 20, in their respective directions of rotation 62, 64, to facilitate an increase in rotational velocity during the onset of tissue cutting, e.g., immediately following the formation of each respective virtual tissue sample aperture 46, to enhance the start of tissue cutting.

Thus, controller 58 may be configured to execute a velocity profile, e.g., motor velocity profile 74, first velocity profile 76 and/or second velocity profile 78, that provides a variable rotational velocity for at least one of outer cannula 18 and inner cannula 20 during continuous simultaneous rotation of outer cannula 18 and inner cannula 20. The velocity profile provides an increase in velocity of at least one of outer cannula 18 and inner cannula 20 as virtual tissue sample aperture 46 begins to close to sever the tissue.

Figure 10:
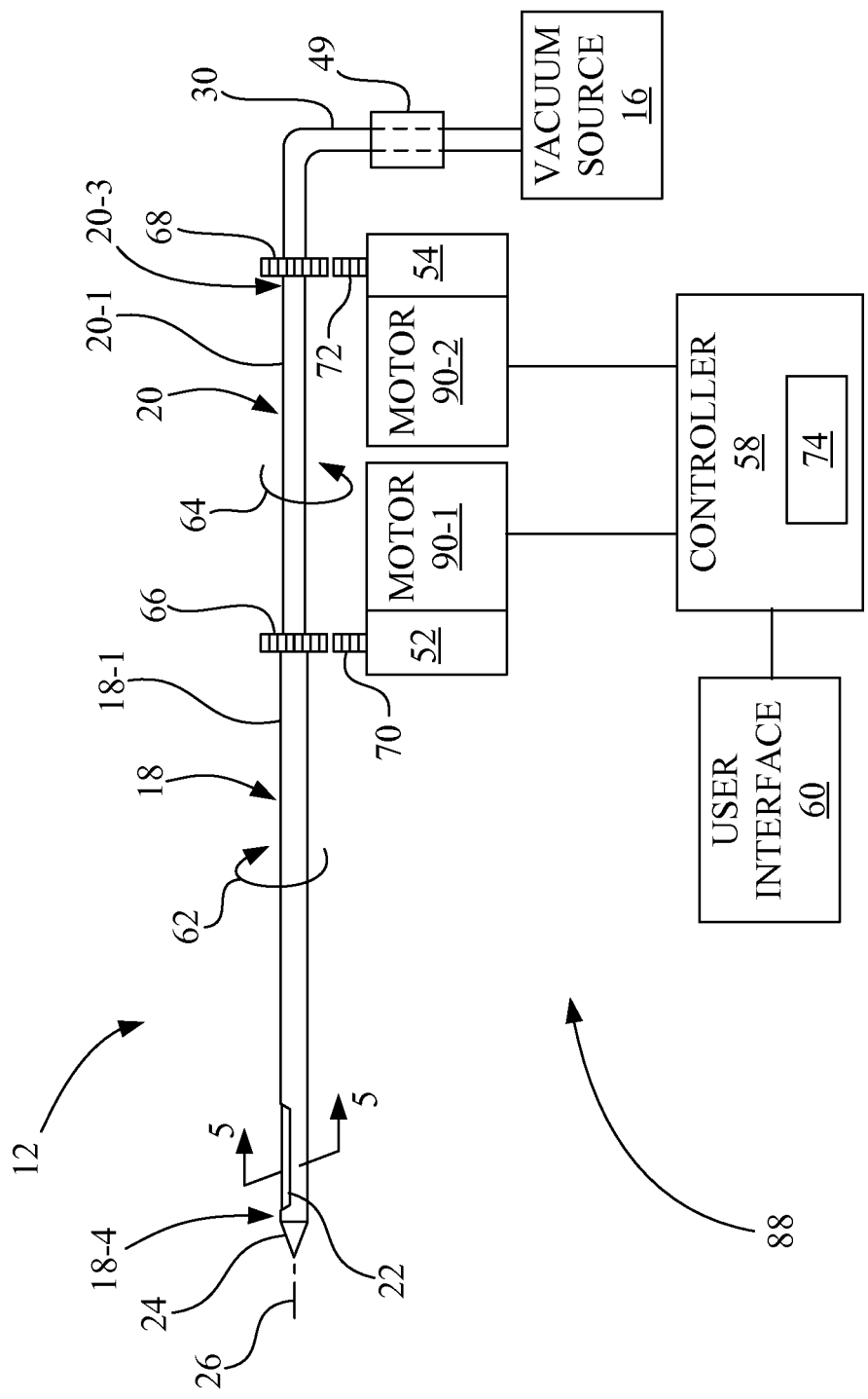
FIG. 10 is a pictorial illustration of another embodiment of a biopsy device including a probe assembly and driver unit, configured in accordance with an embodiment of the present invention.

FIG. 10 shows an alternative embodiment for the driver unit 14 of FIG. 1, and is referenced as driver unit 88. Driver unit 88 differs from driver unit 14 in that first drive mechanism 52 is driven by a first motor 90-1 and second drive mechanism 54 is driven by a second motor 90-2. Each motor 90-1 and 90-2 is separately coupled to controller 58 for independent control thereof, thus facilitating more design options with respect to the velocity profiles used in controlling the rotation of outer cannula 18 and inner cannula 20.

Figure 11:
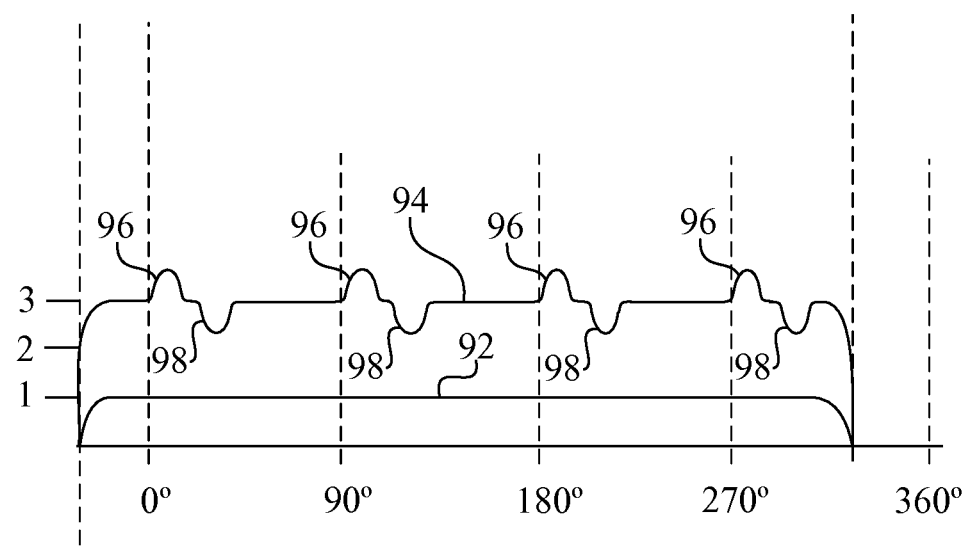
FIG. 11 is a graphical representation of exemplary velocity profiles for the outer cannula and the inner cannula in the embodiment of FIG. 10.

For example, referring also to FIG. 11, controller 58 is configured to control motor 90-1 to effect rotation of outer cannula 18 in accordance with a first velocity profile 92 and is configured to control motor 90-2 to effect rotation of inner cannula 20 in accordance with a second velocity profile 94. On average, as shown in FIG. 11, the velocity magnitude of inner cannula 20 subject to velocity profile 94 is three times the velocity magnitude of outer cannula 18 subject to velocity profile 92, with outer cannula 18 and inner cannula 20 rotating in opposite directions.

In the present example, however, first velocity profile 92 provides for the rotation of outer cannula 18 at a constant velocity. Second velocity profile 94 provides for both acceleration 96, and offsetting deceleration 98, to maintain on average the velocity magnitude of inner cannula 20 at three times the velocity magnitude of outer cannula 18. Accordingly, as illustrated in FIGS. 10 and 11, with further reference to FIG. 8, a complete continuous rotation of outer cannula 18 from initial position 80 to final position 82, and a simultaneous counter rotation of inner cannula at an average of three times the velocity of that of outer cannula 18 from initial position 80 to a final position 82, results in the formation of a plurality of virtual tissue sample apertures 46, which in the present example virtual tissue sample apertures 46-1, 46-2, 46-3 and 46-4 are formed at angular radial positions relative to longitudinal axis 26 offset from one another at 90 degrees of rotation of outer cannula 18, resulting in four samples being harvested within one rotation of outer cannula 18. Thus, in the present example a virtual tissue sample aperture 46-1 is formed at 0 degrees, a virtual tissue sample aperture 46-2 is formed at 90 degrees, a virtual tissue sample aperture 46-3 is formed at 180 degrees and a virtual tissue sample aperture 46-4 is formed at 270 degrees.

Since each motor 90-1 and 90-2 is separately coupled to controller 58 for independent control thereof, and in turn providing independent control of outer cannula 18 and inner cannula 20, the flexibility exists such that the respective velocity profiles for outer cannula 18 and inner cannula 20 may be modified to provide an equal magnitude of velocity for outer cannula 18 and inner cannula 20 as virtual tissue sample aperture 46 begins to close to sever the tissue, if desired.

Also, the flexibility exists such that the respective velocity profiles for outer cannula 18 and inner cannula 20 may be modified to provide a change in rotational velocity of at least one of outer cannula 18 and inner cannula 20 to define a next angular radial position of a next formation of virtual tissue sample aperture 46. For example, changes to the rotational velocities of outer cannula 18 and inner cannula 20 during the absence of a virtual tissue sample aperture, i.e., while the virtual tissue sample aperture is closed, can orient outer cannula 18 and inner cannula 20 to effect a new desired angular radial position of the virtual tissue sample aperture.

Accordingly, in view of the above, those skilled in the art will recognize that by varying the rotational velocity differences between the rotational velocity of outer cannula 18 and the rotational velocity of inner cannula 20, more or less samples may be taken than in the example above. Further, while the example above provides for multiple samples within one revolution of outer cannula 18, velocity profiles may be generated to provide for the harvesting of samples over multiple rotations of outer cannula 18. Also, while in the examples discussed above outer cannula 18 rotates at a slower velocity than inner cannula 20, it is possible to harvest samples using the opposite approach, i.e., with the outer cannula 18 having the higher rotational velocity than inner cannula 20. Still further, while the examples provided above provide for sequential sampling, it is contemplated that more complex velocity profiles may be generated to facilitate non-sequential sampling during one or more rotations of the cannula that has the slower rotational velocity.

Figure 12:
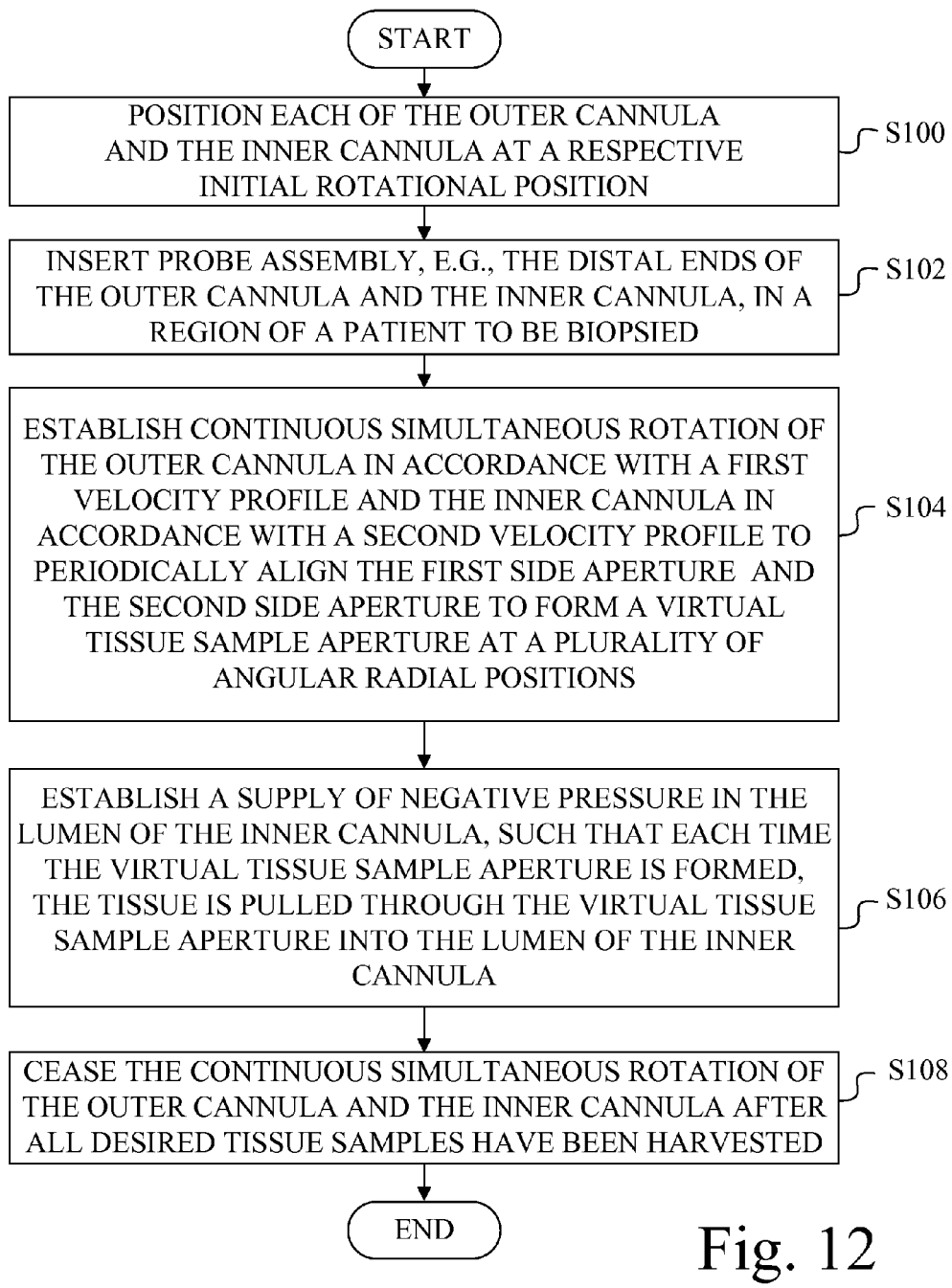
FIG. 12 is a flowchart of a method for controlling a biopsy device, such as the biopsy device of FIG. 1.

FIG. 12 is a flowchart of a method for controlling a biopsy device, such as biopsy device 10, during a biopsy procedure, with reference to the embodiment of FIGS. 1-5.

Figure 5:
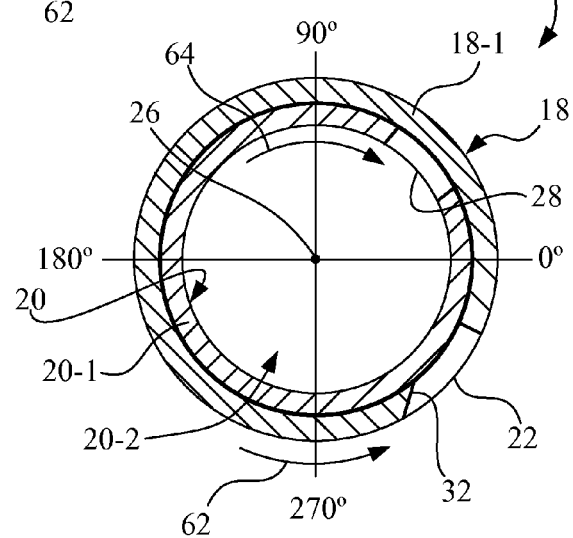
FIG. 5 is a cross-section view of the probe assembly of FIG. 1 taken along line 5-5.

At act S100, each of outer cannula 18 and inner cannula 20 is positioned at a respective initial rotational position 80 (see FIGS. 5 and 9). The respective initial rotational position of outer cannula 18 and inner cannula 20 is selected such that first aperture 22 and second aperture 28 are not in alignment such that the virtual tissue sample aperture is not formed prior to insertion of said probe assembly into the patient.

At act S102, probe assembly 12, e.g., the distal ends of outer cannula 18 and inner cannula 20, is inserted in a region of a patient to be biopsied. The region may be, for example, breast tissue.

At act S104, continuous simultaneous rotation of outer cannula 18 in accordance with a first velocity profile and inner cannula 20 in accordance with a second velocity profile is established to periodically align first side aperture 22 and second side aperture 28 to form a virtual tissue sample aperture 46 at a plurality of angular radial positions relative to longitudinal axis 26 (see FIGS. 4 and 9). In the present embodiment, for example, outer cannula 18 and inner cannula 20 are rotated in opposite rotational directions 62, 64.

At act S106, a supply of negative pressure is established in lumen 20-2 of inner cannula 20, such that each time the virtual tissue sample aperture 46 is formed, tissue 48 is pulled through virtual tissue sample aperture 46 into lumen 20-2 of inner cannula 20, as illustrated in FIG. 4, and thereafter first side aperture 22 and second side aperture 28 cooperate to sever tissue 48 that is pulled into inner cannula 20 as virtual tissue sample aperture 46 is closed by the continuous simultaneous rotation of the outer cannula 18 and inner cannula 20 (see, e.g., FIG. 5 depicting a closed orientation). The supply of negative pressure may be continuous or intermittent. Thus, advantageously, biopsy device 10 severs the tissue sample during the tissue sample acquisition process. Each tissue sample so severed is transported through lumen 20-2 of inner cannula 20 by the negative pressure provided by vacuum source 16 to tissue sample receptacle 49.

At act S108, the continuous simultaneous rotation of outer cannula 18 and inner cannula 20 is ceased after all desired tissue samples have been harvested. The end of the continuous simultaneous rotation of outer cannula 18 and inner cannula 20 is selected to coincide with a final position 82 (see FIGS. 5 and 9) wherein first side aperture 22 and second side aperture 28 are not in alignment, such that prior to removal of probe assembly 12 from the patient the virtual tissue sample aperture 46 is not again formed.

While this invention has been described with respect to embodiments of the invention, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
   a probe assembly including:
      a first cannula having a first side wall defining a first lumen, said first cannula having a first proximal end and a first distal end, said first cannula having a first aperture extending through said first side wall to said first lumen proximal to said first distal end, said first cannula having a longitudinal axis, and
      a second cannula having a second side wall defining a second lumen, said second cannula having a second proximal end and a second distal end, said second cannula having a second aperture extending through said second side wall to said second lumen proximal to said second distal end, said second cannula being disposed co-axially with said first cannula,
      at least one of said first aperture and said second aperture having a cutting edge; and
   a driver unit configured for releasably mounting said probe assembly, said driver unit being operatively configured to simultaneously rotate said first cannula and said second cannula in opposite rotational directions at different rotational velocities so that said first aperture and said second aperture periodically come into alignment to form a virtual tissue sample aperture.

2. The biopsy device of claim 1, said first cannula being an outer cannula having a needle tip located at said first distal end, and said second cannula being an inner cannula positioned in said first lumen of said outer cannula, said biopsy device further comprising a vacuum source in fluid communication with the inner cannula to pull tissue by negative pressure into said inner cannula each time said virtual tissue sample aperture is formed, said first aperture and said second aperture cooperating to sever said tissue that is pulled into said inner cannula as said virtual tissue sample aperture is closed by continued rotation of said outer cannula and said inner cannula.

3. The biopsy device of claim 1, wherein said virtual tissue sample aperture is formed at a plurality of angular radial positions relative to said longitudinal axis during a biopsy procedure by continuous simultaneous rotation of both of said first cannula and said second cannula.

4. The biopsy device of claim 3, wherein said second cannula is positioned in said first lumen of said first cannula, said biopsy device further comprising a vacuum source in fluid communication with the second cannula to provide a supply of negative pressure in said second lumen of said second cannula, and wherein during a biopsy procedure each time said virtual tissue sample aperture is formed tissue is pulled into said second lumen of said second cannula, and thereafter said first aperture and said second aperture cooperating to sever said tissue that is pulled into said inner cannula as said virtual tissue sample aperture is closed by said continuous simultaneous rotation of said first cannula and said second cannula, each tissue sample so severed being transported through said second lumen of said second cannula by said negative pressure to a tissue sample receptacle.

5. The biopsy device of claim 4, said driver unit including a controller configured to execute a velocity profile that provides a variable rotational velocity for at least one of said first cannula and said second cannula during said continuous simultaneous rotation of said first cannula and said second cannula.

6. The biopsy device of claim 5, wherein said velocity profile provides an increase in velocity of at least one of said first cannula and said second cannula as said virtual tissue sample aperture begins to close to sever said tissue.

7. The biopsy device of claim 5, wherein said velocity profile provides an equal magnitude of velocity for said first cannula and said second cannula as said virtual tissue sample aperture begins to close to sever said tissue.

8. The biopsy device of claim 5, wherein said velocity profile provides a change in rotational velocity of at least one of said first cannula and said second cannula to define a next angular radial position of a next formation of said virtual tissue sample aperture.

9. The biopsy device of claim 1, said driver unit including a controller configured to execute a velocity profile that provides a variable rotational velocity for at least one of said first cannula and said second cannula during the simultaneous rotation of said first cannula and said second cannula.

10. The biopsy device of claim 9, wherein said velocity profile provides an increase in rotational velocity of at least one of said first cannula and said second cannula as said virtual tissue sample aperture begins to close.

11. The biopsy device of claim 9, wherein said velocity profile provides an equal magnitude of velocity for said first cannula and said second cannula as said virtual tissue sample aperture begins to close.

12. The biopsy device of claim 9, wherein said velocity profile provides a change in rotational velocity of at least one of said first cannula and said second cannula to define a next angular radial position of a next formation of said virtual tissue sample aperture.

13. The biopsy device of claim 1, said driver unit including:
   a first drive mechanism configured for drivable engagement with the first cannula to rotate said first cannula at a first rotational velocity in a first rotational direction; and
   a second drive mechanism configured for drivable engagement with the second cannula, said second drive mechanism being configured to rotate said second cannula at a second rotational velocity different from said first rotational velocity in a second rotational direction, opposite to said first rotational direction, simultaneously with the rotation of said first cannula.

14. The biopsy device of claim 13, wherein said first drive mechanism and said second drive mechanism has a motor associated therewith, said driver unit further including a controller communicatively coupled to said motor, said controller being configured to control said motor to effect rotation of said first cannula in accordance with a first velocity profile and to effect rotation of said second cannula in accordance with a second velocity profile.

15. The biopsy device of claim 13, wherein said first driving mechanism has a first motor and said second driving mechanism has a second motor, said driver unit further including a controller communicatively coupled to said first motor and said second motor, said controller being configured to control said first motor to effect rotation of said first cannula in accordance with a first velocity profile and to control said second motor to effect rotation of said second cannula in accordance with a second velocity profile.

16. The biopsy device of claim 1, comprising:
a first gear fixedly attached to said first cannula for rotation about said longitudinal axis;
a second gear fixedly attached to said second cannula for rotation about said longitudinal axis; and
said drive unit including:
a first gear drive mechanism engaged said first gear;
a second gear drive mechanism engaged with said second gear;
a motor drivably coupled to each of said first gear drive mechanism and said second gear drive mechanism; and
a controller communicatively coupled to said motor, said controller being configured to control said motor to effect rotation of said first cannula in accordance with a first velocity profile and to effect rotation of said second cannula in accordance with a second velocity profile.

17. The biopsy device of claim 1, wherein a longitudinal extent of said first aperture is parallel to said longitudinal axis, and a longitudinal extent of said second aperture is parallel to said longitudinal axis, such that a maximum opening size of said virtual tissue sample aperture is equal to the smaller of a respective opening size for each of said first aperture and said second aperture.

18. The biopsy device of claim 17, wherein at least said first aperture is elliptical and said cutting edge is formed along said longitudinal extent of said first aperture.

19. The biopsy device of claim 1, wherein a longitudinal extent of said first aperture is angled in a first direction relative to said longitudinal axis, and a longitudinal extent of said second aperture is angled in a second direction relative to said longitudinal axis that intersects said first direction, such that a maximum opening size of said virtual tissue sample aperture is less than an opening size of either of said first aperture and said second aperture.

20. The biopsy device of claim 19, wherein said cutting edge is formed along said longitudinal extent of said first aperture.

21. A biopsy device, comprising:
a probe assembly including:
a first cannula having a first side wall defining a first lumen, said first cannula having a first proximal end and a first distal end, said first cannula having a first aperture extending through said first side wall to said first lumen proximal to said first distal end, said first cannula having a longitudinal axis, and
a second cannula having a second side wall defining a second lumen, said second cannula having a second proximal end and a second distal end, said second cannula having a second aperture extending through said second side wall to said second lumen proximal to said second distal end, said second cannula being disposed co-axially with said first cannula, at least one of said first aperture and said second aperture having a cutting edge; and
a driver unit configured for releasably mounting said probe assembly, said driver unit being operatively configured to rotate said first cannula in accordance with a first velocity profile and said second cannula in accordance with a second velocity profile to periodically align said first aperture and said second aperture to form a virtual tissue sample aperture at a plurality of angular radial positions relative to said longitudinal axis during a biopsy procedure by continuous simultaneous rotation of both of said first cannula and said second cannula.

22. The biopsy device of claim 21, wherein said first cannula and said second cannula are rotated in opposite rotational directions.

23. The biopsy device of claim 21, wherein said second cannula is positioned in said first lumen of said first cannula, said biopsy device further comprising a vacuum source in fluid communication with the second cannula to provide a source of negative pressure in said second lumen of said second cannula, and wherein during said biopsy procedure each time said virtual tissue sample aperture is formed tissue is pulled into said second lumen of said second cannula, and thereafter said first aperture and said second aperture cooperating to sever said tissue that is pulled into said inner cannula as said virtual tissue sample aperture is closed by said continuous simultaneous rotation of said first cannula and said second cannula, each tissue sample so severed being transported through said second lumen of said second cannula by said negative pressure to a tissue sample receptacle.

24. A method for controlling a biopsy device during a biopsy procedure, said biopsy device having a probe assembly with an outer cannula having a distal needle tip and an inner cannula arranged coaxial with said outer cannula with respect to a longitudinal axis, said outer cannula having a first side aperture and said inner cannula having a second side aperture with at least one of said first side aperture and said second side aperture having a cutting edge, and a vacuum source connected in fluid communication with a lumen of said inner cannula and with a tissue sample receptacle, comprising:
positioning each of said outer cannula and said inner cannula at a respective initial rotational position;
inserting said probe assembly in a region of a patient to be biopsied;
establishing continuous simultaneous rotation of said outer cannula in accordance with a first velocity profile and said inner cannula in accordance with a second velocity profile to periodically align said first side aperture and said second side aperture to form a virtual tissue sample aperture at a plurality of angular radial positions relative to said longitudinal axis;
establishing a supply of negative pressure in said lumen of said inner cannula, such that each time said virtual tissue sample aperture is formed tissue is pulled through said virtual tissue sample aperture into said lumen of said inner cannula, thereafter said first side aperture and said second side aperture cooperate to sever said tissue that is pulled into said inner cannula as said virtual tissue sample aperture is closed by said continuous simultaneous rotation of said outer cannula and said inner cannula, each tissue sample so severed being transported through said lumen of said inner cannula by said negative pressure to a tissue sample receptacle; and
ceasing said continuous simultaneous rotation of said outer cannula and said inner cannula after all desired tissue samples have been harvested.

25. The method of claim 24, wherein said outer cannula and said inner cannula are rotated in opposite rotational directions.

26. The method of claim 24, wherein said respective initial rotational position of said outer cannula and said inner cannula is selected such that said first side aperture and said second side aperture are not in alignment such that said virtual tissue sample aperture is not formed prior to insertion of said probe assembly into said patient.

27. The method of claim 24, wherein said continuous simultaneous rotation said outer cannula and said inner cannula is selected to coincide with a final position wherein said first side aperture and said second side aperture are not in alignment, such that said virtual tissue sample aperture is not again formed prior to removal of said probe assembly from said patient.

* * * * *